United States Patent [19]

Speiser et al.

[11] Patent Number: 5,187,150

[45] Date of Patent: Feb. 16, 1993

[54] POLYESTER-BASED COMPOSITION FOR THE CONTROLLED RELEASE OF POLYPEPTIDE MEDICINAL SUBSTANCES

[75] Inventors: Peter Speiser; Urs Schleuniger, both of Zurich; Piero Orsolini; Frédéric Heimgartner, both of Martigny, all of Switzerland

[73] Assignee: Debiopharm S.A., Lausanne, Switzerland

[21] Appl. No.: 503,066

[22] Filed: Mar. 29, 1990

Related U.S. Application Data

[63] Continuation of Ser. No. 255,936, Oct. 11, 1988, abandoned.

[30] Foreign Application Priority Data

Oct. 14, 1987 [CH] Switzerland .......................... 4022/87

[51] Int. Cl.$^5$ .......................... A61K 37/02; A61K 9/58
[52] U.S. Cl. .......................... 514/2; 424/426; 424/457; 424/459; 424/489; 424/490; 424/491; 427/3; 514/3; 514/12; 514/15; 514/21; 514/885; 514/886; 514/866; 514/963; 514/965
[58] Field of Search .................. 424/78, 80, 426, 457, 424/459, 489, 490, 491; 427/3; 514/2, 3, 15, 21, 885, 886, 866, 963, 965

[56] References Cited

U.S. PATENT DOCUMENTS

| | | | |
|---|---|---|---|
| 3,909,444 | 9/1975 | Anderson et al. | 427/3 |
| 3,978,203 | 8/1976 | Wise | 424/425 |
| 4,186,189 | 1/1980 | Shalaby et al. | 424/78 |
| 4,481,353 | 11/1984 | Nyilas | 528/303 |
| 4,594,407 | 6/1986 | Nyilas et al. | 528/302 |
| 4,652,441 | 3/1987 | Okada et al. | 264/4.6 |
| 4,675,189 | 6/1987 | Kent et al. | 424/426 |
| 4,687,676 | 8/1987 | Wu et al. | 427/3 |
| 4,711,782 | 12/1987 | Okada et al. | 424/455 |
| 4,741,872 | 5/1988 | De Luca et al. | 428/402.22 |
| 4,767,628 | 8/1988 | Hutchinson | 514/12 |
| 4,828,840 | 5/1989 | Sakamoto et al. | 427/3 |
| 5,025,004 | 6/1991 | Wu et al. | 427/3 |
| 5,081,031 | 1/1992 | Tsilibary et al. | 623/22 |
| 5,116,368 | 5/1992 | McCarthy et al. | 623/22 |

FOREIGN PATENT DOCUMENTS 7800011 12/1978 PCT Int'l Appl. .

Primary Examiner—Ronald W. Griffin
Attorney, Agent, or Firm—Pennie & Edmonds

[57] ABSTRACT

The pharmaceutical composition is intended in particular for the sustained and controlled release of an effective dose of a medicinal substance. It comprises, as a carrier for the medicinal substance, a biodegradable polymer or copolymer or a mixture of biodegradable polymers and/or copolymers derived from a dicarboxylic acid selected from the acids of the Krebs cycle, and from an aliphatic diol containing 4 carbon atoms or from cyclohexane-1,4-dimethanol.

21 Claims, No Drawings

POLYESTER-BASED COMPOSITION FOR THE CONTROLLED RELEASE OF POLYPEPTIDE MEDICINAL SUBSTANCES

This is a continuation of application Ser. No. 07/255,936, filed Oct. 11, 1988, now abandoned.

The present invention relates to a pharmaceutical composition and more particularly to a composition permitting the sustained and controlled release of an effective dose of a given polypeptide or polypeptide derivative medicinal substance.

There are numerous examples of therapeutic treatments in which it is desirable to achieve, by means of a single administration, a sustained release of the medicinal substance over a period of time and a controlled release as regards the dose passing into the organism. Various solutions have already been proposed in this field, such as subcutaneous implants or injectable suspensions of microparticles or microcapsules. Such compositions are based on biocompatible and biodegradable polymers, for example polymers or copolymers of D,L-lactic acid and/or glycolic acid (see e.g. European patent applications A-0052510 and A-0058481).

In practice, interesting results have been obtained from therapeutic treatments with polypeptides, such as LHRH or its analogues, used in the form of injectable microcapsules or microparticles based on a D,L-lactic acid/glycolic acid copolymer (approx. 50:50) with an average molecular weight of the order of about 50,000. As this type of copolymer hydrolyzes relatively easily in vivo, it is essential to use forms of high molecular weight: the synthesis of such copolymers requires the use of organometallic polymerization catalysts and, when the reaction is complete, it is imperative for all traces of these catalysts to be removed for toxicological reasons. Operations of this kind are often very lengthy and very expensive.

More generally, it is found that the techniques of polymerization without the use of organometallic catalysts are rather unsuitable for the preparation of biodegradable polymers with an average molecular weight of the order of 30,000 or more.

Moreover, in order to prevent this type of polymer (lactide/glycolide copolymer) from being degraded too quickly by hydrolysis in vivo, one is forced to prepare injectable microcapsules or microparticles of relatively large mean size: when these are injected, the tissues are very often observed to give an inflammatory response, which is sometimes extremely painful for the subject treated.

It has furthermore been found in some cases that the uniformity of release of a peptide-type medicinal substance in the form of microparticles (see e.g. European patent application A-0058481) gives rise to problems, especially where the phenomenon of two-stage release is to be avoided.

The pharmaceutical industry is therefore always looking for biodegradable polymers which are capable of being used as carriers for medicinal substances, especially for a sustained and controlled release of the active substance, and which do not have the above-listed disadvantages inherent in the biodegradable polymers recommended to date. The present invention offers an advantageous solution to this problem, which is defined in claim 1.

In fact, certain polyesters or copolyesters are known which are derived from carboxylic acids of the Krebs cycle, such as, for example, succinic, malic, fumaric or oxaloacetic acids, and from polyols such as triols like glycerol, mannitol or sorbitol: according to U.S. Pat. No. 3,978,203, they can be used inter alia as carriers for medicinal substances, mainly steroids, in the form of matrices. However, the polyesters described have a relatively high average molecular weight of between about 20,000 and 200,000. U.S. Pat. No. 4,481,353 recommends the use of polyesters derived from acids of the Krebs cycle, such as those mentioned above, and from $C_2$ to $C_8$ aliphatic diols in the preparation of surgical requisites such as, for example, microtubes, ligatures or sutures. In the said patent, however, there is no mention or suggestion of the use of this type of polyester as a carrier for medicinal substances.

The present invention relates to a well-defined class of polyesters or copolyesters which can advantageously be used for the stated purpose. More particularly, they are biodegradable polyesters or copolyesters or mixtures of biodegradable polyesters and/or copolyesters derived from a dicarboxylic acid selected from the acids of the Krebs cycle, and from an aliphatic diol containing 4 carbon atoms or from cyclohexane-1,4-dimethanol. Fumaric or succinic acid is preferably used as the dicarboxylic acid of the Krebs cycle and butane-1,4-diol or butane-2,3-diol is preferably used as the $C_4$ aliphatic diol, apart from cyclohexane-1,4-dimethanol.

According to the invention, it is advantageously possible to use a polyester such as poly-1,4-butylene succinate, poly-1,4-butylene fumarate, poly-1,4-cyclohexanedimethylene succinate or fumarate or else poly-2,3-butylene succinate or fumarate. The above-mentioned polyesters can be used in the pure state or in the form of mixtures of at least two of the said polyesters. According to the invention, it is also possible to use a copolyester derived from fumaric and succinic acids and from butane-1,4-diol or butane-2,3-diol, for example. A copolyester derived from fumaric acid and from butane-1,4-diol and butane-2,3-diol can also be used. Interesting results have been obtained using poly-1,4-butylene succinate, poly-1,4-cyclohexanedimethylene succinate and poly-2,3-butylene fumarate, although this list does not imply a limitation.

In a particular embodiment of the invention, a further possibility is to use one of the above-mentioned polyesters mixed with a polyester or copolyester derived from an alpha-hydroxycarboxylic acid such as D- or L-lactic acid and from glycolic acid. Interesting results have been obtained using mixtures of poly-1,4-butylene succinate and D,L-lactide/glycolide polyester.

The polyesters, used according to the present invention are characterized by a relatively low weight average molecular weight which is more generally between about 2,000 and 50,000 and preferably less than 10,000. This has a decisive advantage when it comes to their synthesis, which can be carried out without any need to use organometallic polymerization catalysts. They can easily be obtained by means of the customary techniques such as melt phase polymerization in the presence of an organic esterification catalyst (e.g. p-toluenesulphonic acid), or pearl phase polymerization.

The polyesters obtained by these methods are characterized by a lipophilic behaviour which is more pronounced than that of the lactic or glycolic acid polymers or copolymers known hitherto; they are also less sensitive than the latter to degradation by hydrolysis. This feature makes it possible easily to achieve one of the stated aims, namely to prepare injectable microcapsules or microparticles with very small dimensions of the order of only a few microns or tens of microns.

The polyesters mentioned above, or mixtures thereof, are suitable for the preparation of any form of carrier for medicinal substances: a matrix in which the active substance is dispersed or solubilized can be considered for this purpose, examples being beads, implants, microspheres or microparticles. These polyesters or mixtures thereof are particularly suitable for carrying out the techniques of microencapsulation of active substances, such as microencapsulation by phase separation or microencapsulation by evaporation (solvent evaporation microencapsulation). To obtain the carriers in the appropriate form, it is also possible to use processes such as spray drying or spray congealing, which both produce microparticles containing the active substance, or alternatively extrusion, which makes it possible to prepare implants of predetermined shape. These are known techniques: some of them will be described in greater detail in the Examples below.

Microcapsules are preferably prepared using polyesters with a weight average molecular weight of the order of about 2,000 to 5,000, for example of the order of about 2,500. In a particular embodiment of the invention, a polyester of this type is used in a mixture with a D,L-lactic/glycolic acid copolyester (approx. 50:50) with an average molecular weight of between about 35,000 and 60,000, preferably of the order of about 45,000. However, this is not an exhaustive list.

Depending on the particular case, it is also possible to incorporate into the polyester composition a biocompatible hydrolysis modifier such as a carboxylic acid, like citric acid, or else a salt such as sodium chloride (neutral) or sodium carbonate (alkaline).

Despite their lipophilic character mentioned earlier, the polyesters forming the subject of the present invention have a sufficient affinity for hydrophilic medicinal substances such as polypeptides. Examples of medicinal substances which may be used are natural or synthetic polypeptides containing from 3 to 60 amino acid units, or else a polypeptide derivative such as a non-toxic salt of a polypeptide. For example, it may be advantageous to use a decapeptide such as luteinizing hormon/follicle-stimulating hormone releasing hormone (LH/FSH-RH) or one of its natural or synthetic analogues, or else thyrotropin releasing hormone (TRH), insulin, somatostatin or one of its synthetic analogues, human or animal calcitonin, human or animal growth hormone, growth hormone releasing hormone (GHRH), a cardiopeptide such as ANP (human 1-28) or a natural or recombinant interferon. Such active substances are suitable for the various microencapsulation techniques.

More generally, the polypeptide or polypeptide derivative medicinal substances which can advantageously be used in the preparation of compositions according to the invention can be selected from substances having an antiinflammatory, antitumoral, immunosuppressive, antithrombotic, neuroleptic, antidepressant or antihypertensive effect or a non-toxic salt of such substances. This is not an exhaustive list.

As a general rule, the pharmaceutical compositions according to the invention contain the chosen polypeptide or polypeptide derivative medicinal substance in a proportion of about 0.5 to 20% by weight, although these limits can be exceeded in particular cases. One of the preferred forms of such compositions consists of injectable microcapsules or microparticles with a mean size of between about 1 and 500 microns, dispersed in a vehicle intended for parenteral injection.

When administered in vivo or placed in an aqueous environment of physiological type, the pharmaceutical composition according to the invention releases the medicinal substance into the surrounding medium at a constant rate over a period of at least 1 week.

The Examples below serve to illustrate the present invention without thereby implying a limitation.

EXAMPLE 1

Preparation of a succinic acid polyester 29.25 g (0.25 mol) of succinic acid were mixed with 22.53 g (0.25 mol) of butane-1,4-diol, 0.43 g of p-toluenesulphonic acid (1% by weight, based on the theoretical yield of polyester) and 90 ml of toluene, the mixture being placed in a reactor equipped with a magnetic stirrer, a thermometer, a means for introducing inert gas ($N_2$) and a water separator. The reaction mixture was heated to 110° C. and, after 10 hours of heating, a first sample of polymer was taken in order to determine its intrinsic viscosity (I.V.). Samples were taken at regular intervals until the I.V. index had reached 0.34 (measured at 25° C. in chloroform): heating was stopped at that point and the reaction mixture was left to cool to room temperature, with stirring.

EXAMPLE 2

Preparation of a succinic acid polyester 47.24 g (0.40 mol) of succinic acid were mixed with 60.57 g (0.42 mol) of cyclohexane-1,4-dimethanol, the mixture being placed in a reactor equipped with a magnetic stirrer, a thermometer and a distillation bridge fitted to a means for introducing inert gas ($N_2$) and to a vacuum pump. With the reaction mixture placed under an inert atmosphere, the temperature was gradually raised to 130° to 170° C. over a period of 22 h and then kept at 180° C. under a pressure of 1 mm Hg. After 72 h of heating at this temperature and cooling to about 25° C., the desired polymer was collected; it had an I.V. index of 0.27 (measured at 25° C. in chloroform).

EXAMPLE 3

Preparation of a fumaric acid polyester 34.83 g (0.3 mol) of fumaric acid were mixed with 28.4 g (0.315 mol) of butane-2,3-diol and the mixture was placed in a reactor identical to that described in Example 2. With the reaction mixture placed under an inert atmosphere, the temperature was gradually raised to 130° to 180° C. over 6 h and then kept at 170°–180° C. for 20 h under a pressure of 5 mm Hg. The desired polymer was thus collected and had a weight average molecular weight of about 2,000 (measurement of the vapour pressure by osmometry).

EXAMPLE 4

Preparation of a polyester-based pharmaceutical composition by microencapsulation 0.10 g of a decapeptide of the formula (pyro)Glu-His-Trp-Ser-Tyr-D-Trp-Leu-Arg-Pro-Gly-$NH_2$ (hereafter called LHRH-D-Trp$_6$) was suspended in a solution of 2.0 g of poly-1,4-butylene succinate (I.V. Index 0.35; see Example 2) in 100 ml of methylene chloride. The suspension obtained was then emulsified with a solution of 1.35 g of methyl cellulose in 500 ml of distilled water (rotation speed 1,900 rpm) and the organic solvent was then removed by rotary evaporation (rotation speed 470 rpm) for 2 h at 40° C. under a pressure of 380 mm Hg. The resulting microcapsules were then filtered off, washed with cold H₂O and finally dried under vacuum.

EXAMPLE 5

Preparation of a polyester-based pharmaceutical composition by microencapsulation 0.037 g of LHRH-D-Trp$_6$ was suspended in a solution of 1.0 g of poly-1,4-butylene succinate weight average molecular weight 2600) in 36 ml of methylene chloride, and 30 ml of silicone oil were then added gradually to the suspension, at a rate of about 5 ml/min, at room temperature. The resulting suspension, containing the embryonic microcapsules, was then poured, with thorough stirring, into 3000 ml of 1,1,2-trichlorotrifluoroethane (FREON 113) kept at room temperature. After 5 min of stirring, the resulting microcapsules were filtered off and then dried under vacuum.

Analysis of the microcapsules obtained by this method showed that they were totally devoid of all traces of residual solvent, especially FREON 113. By way of comparison, a solvent residue of at least 5% by weight is observed in the preparation of microcapsules from D,L-lactide/glycolide copolyester under identical conditions.

EXAMPLE 6

Preparation, by microencapsulation, of a pharmaceutical composition based on a mixture of polyester and copolyester 0.037 g of LHRH-D-Trp$_6$ was suspended in 36 ml of methylene chloride containing the following mixture in solution:

0.40 g of poly-1,4-butylene succinate weight average molecular weight approx. 2600) and 0.60 g of 50:50 D,L-lactide/glycolide copolymer weight average molecular weight approx. 45,000).

After undergoing the treatments described in Example 5, the suspension obtained produced microcapsules having the following characteristics: by means of a solubilization treatment with dimethylformamide, it was demonstrated that the D,L-lactide/glycolide copolyester formed the core of the microcapsules and that the poly-1,4-butylene succinate formed the outer wall of these microcapsules.

Furthermore, it was observed that the dried microcapsules had a better flow property than comparable microcapsules prepared either from D,L-lactide/glycolide copolyester on its own or from poly-1,4-butylene succinate on its own.

Comparable results were obtained using mixtures containing 0.20 or 0.30 g of poly-1,4-butylene succinate weight average molecular weight approx. 2600) and 0.80 or, respectively, 0.70 g of 50:50 D,L-lactide/glycolide copolyester weight average molecular weight approx. 45 000).

EXAMPLE 7

Determination of the activity of a pharmaceutical composition in the form of microcapsules These experiments were carried out using microcapsules of LHRH-D-Trp$_6$ prepared by the process of Example 5 and appropriately dried and sterilized.

The microcapsules were injected into rats (laboratory subjects) at a rate of 300 micrograms/kg, in the form of a sterile aqueous suspension (1% TWEEN/2% NaCMC). The LHRH-D-Trp$_6$ released and the testosterone were determined in the blood by radioimmunoassay according to the standard techniques. The results obtained are collated in the Table below (measurements made on 4 subjects).

| Period (days) | LHRH-D-Trp$_6$ (ng/ml) | Testosterone (ng/ml) |
| --- | --- | --- |
| 0 | 0.05 | 3.58 |
| 0.25 | 7.09 | not determined |
| 2 | 1.53 | 7.15 |
| 4 | 0.32 | 1.25 |
| 7 | 0.28 | 1.13 |
| 11 | 0.23 | 1.07 |
| 14 | 0.07 | 1.40 |
| 18 | 0.06 | 1.72 |
| 21 | 0.07 | 1.55 |
| 25 | 0.07 | 2.40 |

After an initial stimulation phase (initial burst effect), the LHRH-D-Trp$_6$ is released continuously and at a constant rate up to day 11 and even beyond. The testosterone decreases and reaches a castration level as from day 4; this castration level is maintained up to day 21.

We claim:

1. A pharmaceutical composition which comprises a polypeptide, a polypeptide derivative or a non-toxic salt thereof, and, as a carrier, a polyester or copolyester or a mixture thereof having a weight average molecular weight of between about 2,000 and 10,000 and being the esterification product of fumaric or succinic acid with an aliphatic diol containing 4 carbon atoms or cyclohexane-1,4-dimethanol.

2. A composition according to claim 1 characterized in that the C$_4$ aliphatic diol is selected from butane-1,4-diol and butane-2,3-diol.

3. A composition according to claim 1 characterized in that the mixture of polyesters or copolyesters comprises at least one polyester or copolyester derived from a dicarboxylic acid selected from fumaric acid and succinic acid, and from a diol selected from butane-1,4-diol, butane-2,3-diol and cyclohexane-1,4-dimethanol, and at least one lactic or glycolic acid polyester or copolyester.

4. A composition according to claim 3, characterized in that the lactic acid or glycolic acid polyester or copolyester has a weight average molecular weight of between 35,000 and 60,000 and represents from 60 to 80% by weight of the mixture of polyester or copolyesters.

5. A composition according to claim 1, characterized in that it also comprises an agent which modifies the hydrolysis of the polyester.

6. A composition according to claim 1 wherein the polypeptide is luternizing hormone/follicle-stimulating hormone releasing hormone (LH/FSH-RH) or a synthetic analog thereof, thyrotropin releasing hormone (TRH), insulin, somatostatin, human or animal calcitonin, human or animal growth hormone, growth hormone releasing hormone (GHRH), a cardiopeptide, or a natural or recombinant interferon.

7. A composition according to claim 1, characterized in that it contains the polypeptide or polypeptide derivative in a proportion of about 0.5 to 20% by weight.

8. A composition according to claim 1 characterized in that the carrier is in the form of a matrix in which the polypeptide or polypeptide derivative is dispersed or solubilized, or is in the form of microcapsules.

9. A composition according to claim 8, characterized in that it is in the form of injectable microcapsules or microparticles with a mean size of between 1 and 500 microns, dispersed in a solution intended for parenteral injection.

10. A composition according to claim 1 characterized in that, when it is administered in vivo or placed in an aqueous medium of physiological type, it releases the polypeptide or polypeptide derivative into the surrounding medium at a constant rate over a period of at least 1 week.

11. A pharmaceutical composition which comprises a polypeptide, polypeptide derivative or a non-toxic salt thereof, and, as a carrier, a polyester the esterification product of fumaric or succinic acid and butane-1,4-diol, butane-2,3-diol or cyclohexane-1,4-dimethanol, said polyester having a weight average molecular weight of between about 2000 and 5000; the polypeptide or polypeptide derivative being present in a proportion of about 0.5 to 20% by weight of the composition.

12. A pharmaceutical composition which comprises a polypeptide, polypeptide derivative or a pharmaceutically acceptable non-toxic salt thereof and, as a carrier, a polyester derived from the esterification product of fumaric and succinic acid with an aliphatic diol containing 4 carbon atoms or cyclohexane-1,4-dimethanol, said polyester having a weight average molecular weight of between about 2000 and 10,000; the polypeptide or polypeptide derivative being present in a proportion of about 0.5 to 20% by weight of the composition.

13. A composition according to claim 12, wherein the composition further comprises a second polyester derived from at least one of lactic acid or glycolic acid.

14. A composition according to claim 13 wherein the second polyester is a 50:50 lactic acid/glycolic acid copolyester having a weight average molecular weight of between 2000 and 60,000, the esterification product has a weight average molecular weight of between about 2000 and 10,000, and the diol is butane-1,4-diol, butane-1,3-diol or mixtures thereof.

15. The composition of claim 12 wherein the polyester is poly-1,4-butylene succinate, poly-1,4-butylene fumarate, poly-1,4-cyclohexane dimethylene succinate, poly-1,4-cyclohexane dimethylene fumarate, poly-2,3-butylene succinate, poly-2,3-butylene fumarate or mixtures thereof.

16. A pharmaceutical composition which comprises a polypeptide, polypeptide derivative or a non-toxic salt thereof, and, as a carrier, a polyester or copolyester derived from the esterification product of fumaric or succinic acid and one of an aliphatic diol containing 4 carbon atoms or from cyclohexane-1,4-dimethanol, said polyester or copolyester having a weight average molecular weight of between 2,000 and 10,000, said composition being essentially free from measurable amounts of residual solvent from the manufacture of said composition.

17. A composition according to claim 12 wherein the polypeptide is luteinizing hormone/follicle-stimulating hormone (LH/FSH-RH) or a synthetic analog thereof, thyrotropin releasing hormone (TRH), insulin, somatostatin, human or animal calcitonin, human or animal growth hormone, growth hormone releasing hormone (GHRH), a cardiopeptide, or a natural or recombinant interferon.

18. A composition according to claim 1 wherein the medicinal substance is (pyro)Glu-His-Trp-Ser-Tyr-D-Trp-Leu-Arg-Pro-Gly-NH$_2$ (LHRH-D-Trp$_6$) or a non-toxic salt thereof.

19. A composition according to claim 18 wherein the medicinal substance is (pyro)Glu-His-Trp-Ser-Tyr-D-Trp-Leu-Arg-Pro-Gly-NH$_2$ (LHRH-D-Trp$_6$) or a non-toxic salt thereof.

20. A composition according to claim 12 wherein the medicinal substance is (pyro)Glu-His-Trp-Ser-Tyr-D-Trp-Leu-Arg-Pro-Gly-NH$_2$ (LHRH-D-Trp$_6$) or a non-toxic salt thereof.

21. A composition according to claim 16 wherein the medicinal substance is (pyro)Glu-His-Trp-Ser-Tyr-D-Trp-Leu-Arg-Pro-Gly-NH$_2$ (LHRH-D-Trp$_6$) or a non-toxic salt thereof.

* * * * *